United States Patent [19]

Gardner, Jr. et al.

[11] Patent Number: 4,461,290
[45] Date of Patent: Jul. 24, 1984

[54] HEARING PROTECTORS

[75] Inventors: Ross Gardner, Jr.; Robert N. Falco; John P. Stallings, all of Indianapolis, Ind.

[73] Assignee: Cabot Corporation, Kokomo, Ind.

[21] Appl. No.: 445,111

[22] Filed: Nov. 29, 1982

Related U.S. Application Data

[63] Continuation of Ser. No. 185,046, Sep. 8, 1980, abandoned, which is a continuation-in-part of Ser. No. 091,414, Nov. 5, 1979, abandoned.

[51] Int. Cl.³ ............................................. A61F 11/02
[52] U.S. Cl. ................................................ 128/152
[58] Field of Search ............... 128/152, 151; 181/129, 181/130, 131, 135, 325

[56] References Cited

U.S. PATENT DOCUMENTS

| | | | |
|---|---|---|---|
| 2,670,738 | 3/1954 | Gibbons | 128/152 |
| 2,785,675 | 3/1957 | Benkman | 128/152 |
| 2,804,072 | 8/1957 | Genzer | 128/152 |
| 2,858,544 | 11/1958 | Roth | 128/152 |
| 3,016,054 | 1/1962 | Rosenblatt | 128/152 |
| 3,259,128 | 7/1966 | Leight | 128/152 |
| 3,431,370 | 3/1969 | Crosby | 128/152 |
| 3,811,437 | 5/1974 | Gardner, Jr. | 128/152 |
| 3,881,570 | 5/1975 | Lewis | 128/152 |
| 3,895,627 | 7/1975 | Leight | 128/152 |
| 3,899,044 | 8/1975 | Stumpf et al. | 181/135 |
| 4,023,642 | 5/1977 | Korn | 128/152 |
| 4,060,080 | 11/1977 | Akiyama | 128/152 |
| 4,160,449 | 7/1979 | Wade | 128/152 |
| 4,215,683 | 8/1980 | Lundin et al. | 128/152 |
| 4,253,452 | 3/1981 | Powers et al. | 128/152 |

FOREIGN PATENT DOCUMENTS 1355052  5/1974  United Kingdom ............... 128/152

Primary Examiner—Henry J. Recla
Attorney, Agent, or Firm—J. Schuman; R. F. Dropkin

[57] ABSTRACT

There is disclosed herein a hearing protector structure comprising a generally U-shaped spring headband and a pair of ear canal obturating elements articulatingly affixed to the end portions of the headband. The hearing protector of the invention is possessed of the characteristics of light weight and comfort combined with superior sound attenuation performance.

9 Claims, 3 Drawing Figures

HEARING PROTECTORS

RELATED APPLICATIONS

This application is a continuation of application Ser. No. 185,046, filed Sept. 8, 1980 now abandoned which is a continuation-in-part of now abandoned application Ser. No. 091,414, filed Nov. 5, 1979.

BACKGROUND OF THE INVENTION

The present invention relates generally to hearing protection devices and is more particularly concerned with hearing protectors of the type comprising a spring type headband having a pair of ear canal contacting members affixed to the end portions thereof.

Hearing protectors of the type comprising a generally U-shaped spring headband having a pair of inwardly directed ear canal contacting members affixed to the end portions thereof are, per se, known. As compared to hearing protectors of the ear muff type such protectors are generally possessed of the advantages of lighter weight and lower bulk. However, they are often substantially less effective, in terms of their primary purpose, sound attenuation, than their ear muff type counterparts.

Accordingly, it is a principal object of the present invention to provide hearing protectors of the type comprising a generally U-shaped spring headband and ear canal contacting members affixed to the end portions of the headband which are substantially more effective in sound attenuation properties than similar protectors of the prior art.

It is another object of the invention to provide hearing protectors of the aforementioned type which are comfortable to wear while providing excellent sound attenuation properties. It is yet another object of the invention to provide hearing protectors of the aforementioned type having the qualities of low bulk and light weight and which protectors are comfortable to wear while providing excellent sound attenuation properties.

It is still another object of the invention to provide hearing protectors of the aforementioned type in which the ear canal contacting members thereof self-adjust to the ear canals of the wearer.

Other objects and advantages of the present invention will, in part, be obvious and will, in part, appear hereinafter.

SUMMARY OF THE INVENTION

In its broadest aspect, the hearing protector of the invention comprises a generally U-shaped spring headband to each of the opposed end portions of which there is affixed an inwardly projecting ear canal obturating pod of a size and shape adapted for partial insertion into the ear canal. Each pod comprises a soft, compliant, smooth and hollow capsular element which is articulatingly affixed to its respective end portion of the headband. By this construction the ear pods, through the biasing action of the spring headband, are partially urged into the ear canals in obturating relationship therewith.

DESCRIPTION OF THE PREFERRED EMBODIMENTS

Figure 1:
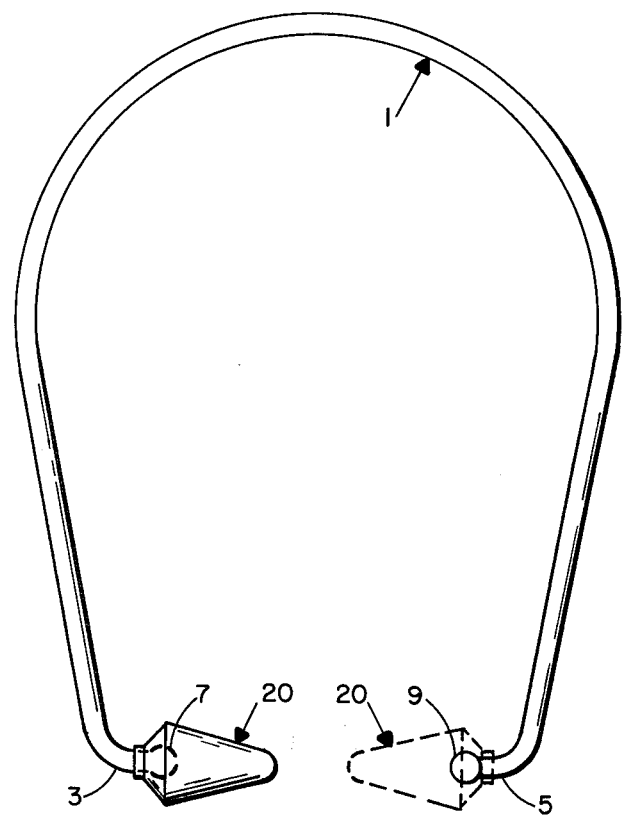
FIG. 1 hereof is a schematic, diagrammatic, partially phantom front view of a hearing protector in accordance with the invention.
Figure 2:
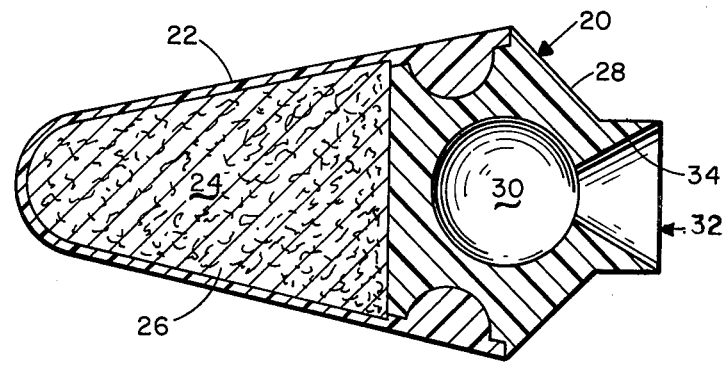
FIG. 2 is a schematic, diagrammatic, longitudinal sectional view of an ear obturating pod 20 of FIG. 1.

Referring now to FIGS. 1 and 2 wherein like reference numerals refer to like structures, the hearing protector of the invention broadly comprises a generally U-shaped spring headband 1 having affixed to each of the opposed end portions 3 and 5 thereof an inwardly directed ear canal obturating pod 20. The fixation of the ear canal obturating pods 20 to said end portions 3 and 5 is achieved in an articulated manner such as to provide said pods with freedom to tilt horizontally and vertically. Each of the pods 20 is comprised of a soft, smooth, compliant and hollow capsular element 22 which is of a size and shape adapted to be partially inserted into the ear canal. Based upon this combination of features the pods 20, under the influence of the spring headband, are urged partially into the ear canals and establish obturating relationships therewith. By reason of the provision of the articulated fixation of the pods 20 to the end portions 3 and 5 of the headband, the pods 20 are free to tilt and conform to the natural angles of the ear canals of the wearer, thereby to inherently seat therein with maximum obturating effect and without need for external adjustment thereof by the wearer. This is an important advantage of the hearing protector of the invention since it is often the case that the ear canals of an individual are not precisely bilaterally symmetrical. In addition, it has been found that prior art hearing protectors often require substantial wearer adjustments of the ear canal contacting members thereof in order to obtain maximum obturating effect and that these adjustments are often improperly or carelessly made or are neglected, thereby not providing the wearer with the maximum hearing protection affordable by the protector. In accordance with the hearing protector of the instant invention, however, these adjustments, which can be of a subtle character, occur automatically.

The major roles of the generally U-shaped headband 1, of course, are to act as a carrier for the ear canal obturating pods 20 and to act as a biasing device to urge said pods 20 into obturating relationships with the ear canals. Bearing these criteria in mind, therefore, the design, construction and materials employable in the fabrication of said headband 1 are obviously subject to considerable variation. The headband 1 can be composed of metallic spring stock and can be of one-piece or multi-piece construction. For example, two curved flat spring elements can be held in interleaved slideable relation, thereby to define an adjustable-length, U-shaped structure. In the interests of light weight and easy one-piece construction, however, it is preferred that the headband 1 be suitably molded of a stiff, resilient, polymeric, preferably thermoplastic, material such as a rigid polyvinylchloride or polyacetal resin. Thus, in this construction there is provided a readily fabricated headband 1 of light weight which, at the same time, possesses sufficient permanent flexural modulus as to enable it to establish and maintain the pods 20 in obturating engagements with the ear canals throughout the service life of the protector construction.

It has been found that the biasing force exerted by the spring headband 1 upon the pods 20 under conditions of use is of consequence inasmuch as said biasing force must be sufficient to result in effective obturation of the ear canals while, at the same time, being insufficient to cause discomfort to the wearer. By virtue of the pod 20 construction of the invention it has been found that this biasing force need not be great, thereby contributing greatly to the property of wearer comfort afforded by the hearing protector of the invention. We have found, for instance, that a suitable bias of the pods 20 is attained when the headband is of such construction and composition that, when the opposed free ends thereof (as defined by balls 7 and 9 in the construction of FIG. 1) are held apart as a spacing of 14.35 cm, there is generated an inwardly directed recovery biasing force of between about 50 and 300 g (0.49 and 2.94N and preferably between about 100 and 200 g (0.98 and 1.96N). Suitable measurement of this recovery biasing force may be conveniently made by holding one end of the headband 1 in a fixed position while the other end thereof is pulled open to the specified distance by means of a spring scale. Similarly, this measurement may also be suitably made by holding one end of the headband 1 in a fixed position while the other end thereof is suspended under said fixed end and is incrementally loaded with known weights until the specified spacing of 14.35 cm is attained. Control of the recovery biasing force can be had by suitable dimensioning of the headband 1, selection of material of construction thereof or combinations of these.

The construction of the ear canal obturating pods 20 is of substantial consequence in the invention, it being essential that said pods be of a size and shape adapted for partial insertion into the ear canals and that at least the ear-insertable portions thereof comprise a smooth, soft, compliant and hollow capsular element 22. In view of these requirements, the capsular element 22 is composed of a soft, smooth and compliant elastomeric or plastomeric material such as plasticized polyvinylchloride, silicone rubber, ethylene/vinyl acetate copolymer, styrene-butadiene block copolymers, ethylenepropylene diene rubber, neoprene rubber, polyurethane rubber, natural rubber and the like. The hardness of the material of construction of the capsular element 22, as determined at room temperature by the Shore A durometer method disclosed in ANSI/ASTM D 2240-75, can be within the range of from about 10 to about 80, and, preferably, will be within the range of from about 20 to about 50.

Preferably, the capsular element 22 will be of conical shape. Of course, employing such a conically shaped capsular element 22, the small diameter end of the element will constitute the insertable free end of the ear canal obturating pod 20 while the large diameter end thereof will define the outboard end for attachment to the end portion 3 or 5 of headband 1. The included angle defined by a conically shaped capsular element 22 may reside within the range of from about 15° to about 45°, the preferred range being from about 20° to about 30°. The small end of a conically shaped capsular element 22 can have a diameter of between about 0.120 and about 0.4 inch (0.3 and 1.02 cm) and will preferably reside within the range of from about 0.2 to about 0.3 inch (0.51 and 0.76 cm).

The space 24 defined by hollow capsular element 22 can be left empty or, preferably, will be filled with a resilient or compliant filler material 26. Where said capsular element 22 is hermetically sealed said filler material 26 can take the form of a fluid such as water, oil or air. Desirably, however, the filler material 26 will be a resilient or compliant solid or semi-solid such as a silicone putty or grease, glass wool, polyester fiber wadding, polyurethane foam, polyvinylchloride foam and the like. A particularly useful material for use as the filler material 26 in the ear protector device of the invention is an extremely plasticized polyvinylchloride foam, the nature of the plasticizer and its concentration being such as to provide the finished foam with the characteristics of slow recovery rate from deformation thereof and low exerted recovery pressure under conditions of deformation.

The wall thickness of the capsular element 22 is subjected to considerable variation and is normally noncritical with respect to the achievement of the benefits of the invention provided that the compliant character thereof is preserved. Generally, said thickness will be between about 0.0005 to about 0.03 inch (0.0013 to 0.076 cm) and, desirably, will reside within the range of from about 0.01 to about 0.02 inch (0.025 to 0.051 cm).

It is another essential of the invention that the ear obturating pods 20 be articulatingly affixed to the end portions 3 and 5 of headband 1 such that said pods 20 can be freely tilted, both horizontally and vertically, under the influence of the recovery biasing force generated by the spring headband 1. Generally speaking, any articulated fixation arrangement which results in the aforementioned freedom of tilting motion of the pods 20 is suitable for use in the construction of the invetion and many such arrangements will suggest themselves to those of skill in the art. For instance, the pods 20 can be affixed to the end portions 3 and 5 of headband 1 by means of springs, hinges, universal joints and the like. Preferably, however, the fixation arrangement employed will be such that the resulting articulation of each of the pods 20 will allow tilting thereof whereby its free end can describe an orbital path in a plane which is about normal to the plane defined by the headband 1. One suitable polymeric hinge arrangement comprises a short, flexible stalk of a polymeric material such as polypropylene or silicone rubber having one end thereof affixed to an end portion 3 or 5 of the headband 1 and the other end thereof offixed to the ear canal obturating pod 20. Another generally suitable articulated fixation arrangement comprises light gauge coil spring having one end thereof affixed to an end portion 3 or 5 and the other end being affixed to said pod 20.

The preferred articulated fixation arrangement will comprise a ball and socket joint such as is depicted in the drawing hereof. In this arrangement end portions 3 and 5 of the headband 1 are provided with terminal balls 7 and 9, respectively. Said balls 7 and 9 can be separate and distinct elements of the headband 1 structure or can be formed integrally therewith. The outboard end of each capsular pod elemet 22 receives therein a closure member 28 having a centrally located socket 30 of a diameter adapted to receive the balls 7 or 9. Desirably, the center point of articulated fixation of pod 20 to the end portion 3 or 5 of headband 1 will occur at or interiorly, rather than exteriorly, of the outboard end of the pod 20. By adherence to this last-mentioned design feature the tendency of pod 20 to fold upon itself under the urging of headband 1 is minimized. In the embodiment of the invention in FIG. 2 hereof, the geometric center of the socket 30, in other words, the center point of the articulated fixation, is located on the plane defined by the outboard end of capsular element 22 and thus lies interiorly of the outboard end of the pod 20. The passageway 32 leading to said socket 30 is internally chamfered such as to define a conical stop surface 34 which, when brought into contact with the surface of the end portion 3 or 5 of headband 1 by tilting of the pod 20, limits further motion of said pod 20. The material of construction employed in the fabrication of the closure member 29 is desirably of sufficient resiliency as to allow receiption of the ball 7 or 9 in socket 30 merely by pressing the ball 7 or 9 thereinto. For this reason, the closure member 28 of pod 20 is preferably formed of a resilient polymeric material which, for purposes of convenience and compatability, can generally be of the same type as that employed in the fabrication of the capsular element 22.

It should be noted that, while the term "headband" is employed herein in relation to the structure of reference numeral 1, said term is not meant to be limiting of the specific manner in which said structure is used. For example, while the hearing protector of the invention can, of course, be worn with the headband 1 thereof positioned directly over the head of the wearer, substantially equal benefits in the use of the protector are afforded when said headband 1 is worn behind the neck or draped under the chin of the wearer. Indeed, in certain instances, such as when the user is also required to wear bulky headgear, a respirator or eye protection, positioning of said headband 1 either behind the neck or under the chin may be required.

Figure 3:
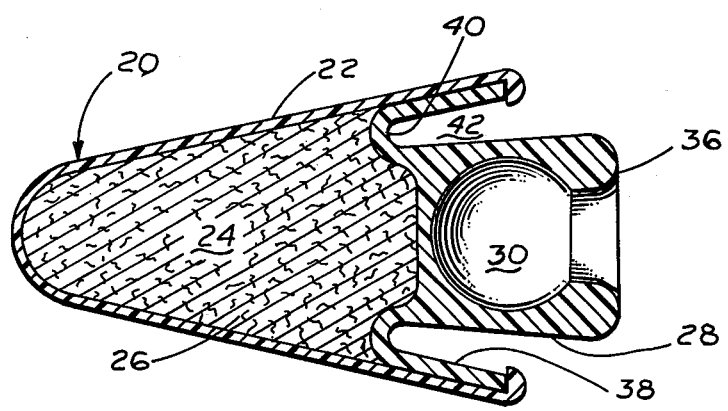
FIG. 3 is a schematic, diagrammatic longitudinal sectional view of another embodiment of the ear obturating pod 20 of FIG. 1.

Another embodiment of the invention is shown in FIG. 3. Shown therein are pod 20, capsular element 22, space 24, filler material 26 and closure member 28. Closure member 28 is comprised of connecting portion 36 and joining portion 38. Connecting portion 36 implements the referred to articulated fixation. Joining portion 38 is for attaching to capsular element 22. Connecting portion 36 and joining portion 38 are separated by section 40 and space 42. Space 42 provides for a more flexible closure member and one which can be grasped and inserted with greater comfort, and in turn a more comfortable pod. Connecting portion 36 and joining portion 38 move into contact with each other when a pod is grasped and inserted into an ear canal.

There follow a number of illustrative non-limiting examples.

EXAMPLE 1

The external elements of two pods 20 of the type shown in FIG. 2 were fabricated in compression molds utilizing a two-part heat cured silicone rubber (Silastic Q-3-9591, manufactured by Dow Corning Corp., Midland, Mich.). Inmold curing was accomplished at a temperature of about 350° F. (177° C.) for about 10 minutes. The Shore A hardness of the cured material, at room temperature, was about 60. The essential dimensions of these external elements were as follows:

CAPSULAR ELEMENT 22

| | |
|---|---|
| Length | 1.028 inch (2.6 cm) |
| Diameter at small end | 0.250 inch (0.64 cm) |
| Diameter at large end | 0.580 inch (1.47 cm) |
| Wall thickness | 0.015 inch (0.04 cm) |
| Included angle | 25° |

CLOSURE MEMBER 28

| | |
|---|---|
| Length | 0.541 inch (1.37 cm) |
| Diameter of socket 30 | 0.250 inch (0.64 cm) |
| Included angle of conical stop surface 34 | 60° |

Spaces 24 of capsular elements 22 were each filled with a cylindrical plug having, in the unconstrained state, a diameter of about 0.54 inch (1.37 cm) and a length of about 0.7 inch (1.8 cm), said plug being composed of a highly plasticized, predominantly closed cell polyvinylchloride foam material. Insertion of the plug was accomplished by first rolling it between the fingers, inserting it into the space 24 and thereafter allowing said plug to expand. Next, the closure member 28 was cemented to the capsular element 22 by means of a room temperature cure silicone rubber cement.

The generally U-shaped headband 1 of this construction was composed of rigid polyvinylchloride and was formed by injection molding of the resin into the shape shown in FIG. 1. The diameter of the resulting molded structure was 3/16 inch (0.48 cm). The radius of curvature of the upper portion of the headband 1 was 2.5 inches (6.35 cm), the length of each of the straight side arm sections thereof was about 3.45 inches (8.76 cm) and the end portions 3 and 5 were each turned inwardly to form an angle of about 85° with respect to the corresponding straight side arm section. The overall length of the headband 1 was 6.3 inches (16 cm). The opposed ends of the formed headband were molded into integral balls 7 and 9 each having a diameter of 0.250 inch (0.64 cms). With the headband 1 in the unconstrained state, the free space between the balls 7 and 9 was about 2.25 inch (5.7 cm). When the balls 7 and 9 of this headband were separated to a distance of 14.35 cm, the recovery biasing force generated was found to be about 180 g (1.7N).

The hearing protector of this example was then assembled by manually seating each of the balls 7 and 9 into a socket 30 of one or the other of the pods 20.

The results of test accomplished utilizing this hearing protector construction are reported in Example 4.

EXAMPLE 2

The elements 22 and 28 of two pods 20 having essentially the same form and dimensions are those described in Example 1 were performed by compression molding of a polyvinylchloride plastisol composition comprising the following ingredients:

| Ingredient | Parts by Weight |
|---|---|
| PVC Resin (Inherent viscosity of 1.11) | 100 |
| Plastolein 9775A ® plasticizer[1] | 65 |
| Di-n-octyl azalate | 25 |
| Calcium-Zinc stabilizer (CZ-10)[2] | 2 |
| Silicone fluid (Dow 200)[3] | 0.5 |
| Epoxidized soybean oil (G-62)[4] | 12 |

[1]Manufactured by Emery Industries, Inc., Cincinnati, Ohio.
[2]Manufactured by Interstab Chemicals, Inc., New Brunswick, New Jersey.
[3]Manufactured by Dow Corning Corp., Midland Michigan.
[4]Manufactured by Rohm and Haas, Philadelphia, Pennsylvania.

The Shore A hardness value of the fused material was about 50. The spaces 24 of the capsular elements 22 were each filled with a polyvinylchloride foam plug of a similar type as that employed in Example 1. The capsular elements 22 were then cemented to the closure members 28 by means of a two-part polyurethane adhesive to complete the two pod 20 constructions.

The headband 1 construction of this example is essentially the same in form and dimensions as that of Example 1. However, in the present example, the headband 1 was produced by injection molding of a polyacetal resin (Delrin ®, manufactured by E. I. duPont de Nemours and Co., Wilmington, Del.). When the ends of the headband were separated to a spacing of 14.35 cm between the balls 7 and 9, the resulting inwardly directed recovery biasing force was determined to be about 142 g (1.4N).

The hearing protector construction was completed by manual assembly of the pods 20 to the headband 1 and the resulting construction tested in accordance with the procedure of Example 4.

EXAMPLE 3

The elements 22 and 28 of a pair of pods 20 were performed by compression molding of a heat cured silicone rubber, SWS-7655, manufactured by SWS Silicones Corp., Adrian, Mich. In-mold curing of the molded elements was accomplished for a period of about 10 minutes and at a temperature of about 350° F. (177° C.). The Shore A durometer value of the cured silicone rubber was about 50. The spaces 24 of capsular elements 22 were filled with polyvinylchloride foam plugs of the type and in the manner employed in Example 1. The capsular elements 22 were then cemented to the closure members 28 utilizing a room temperature cure silicone rubber cement. The completed pods 20, having essentially similar dimensions as those of Examples 1 or 2, were then assembled to a headband 1 of essentially the same dimensions and geometry as those employed in either of Examples 1 or 2. However, in the present example, said headband 1 was formed by injection molding of Celcon ® resin, a highly crystalline acetal copolymer manufactured by Celanese Chemical Co., New York, N.Y. This headband 1, when splayed open to separate the ball elements thereof by a distance of 14.35 cm, resulted in the generation of a recovery biasing force of about 174 g (1.7N).

The resulting hearing protector structure was then tested in accordance with the procedure set forth in Example 4.

EXAMPLE 4

The hearing protectors of Example 1 through 3 were subjected to comparison testing against one another and against several commercially available prior art hearing protectors of a generally similar type. Audiometric data was obtained along with comments elicited from the human test subjects relating to the comfort and ease of use of the hearing protectors employed. Three human subjects were employed for the testing and the tests for each protector repeated three times by each subject. The test subjects were each instructed to adjust the obturating elements of the protectors to the best of his ability in order to maximize the sound attenuation performance of each protector. The audiometric test procedure employed was that of ANSI S3.19, modified only to the extent that three, rather than the stipulated ten, human subjects were employed. For purposes of convenience, the results of the audiometric analyses are reported in Table 1 below as single number Noise Reduction Ratings (NRR). The method of Conversion of ANSI S3.19 audiometic test results to single number NRR ratings is fully disclosed in the monograph: "Single Number Measures of Hearing Protector Noise Reductions", Elliott H. Berger, E-A-RLOG ®, E-A-R Corporation, Indianapolis, Ind., 1979. It should be noted that in each of the prior art hearing protectors the ear canal obturating elements thereof were affixed to the headband element in a non-articulated manner.

TABLE 1

| Hearing Protector | Headband Pressure at 14.35 cm | | NRR (dB) | Subject Comments |
|---|---|---|---|---|
| Prior Art (T) | 80 g | (0.78 N) | 11 | Appears to leak noise despite manual adjustment |
| Prior Art (W-10) | 166 g | (1.63 N) | 15 | Difficult to adjust |
| Prior Art (W-20) | 216 g | (2.12 N) | 15 | Difficult to adjust |
| Prior Art (MSB) | 177 g | (1.73 N) | 16 | Difficult to install and adjust |
| Prior Art (DSS) | 248 g | (2.78 N) | 14 | Extremely uncomfortable |
| Example 1 | 180 g | (1.76 N) | 22 | Self-adjusting |
| Example 2 | 142 g | (1.39 N) | 21 | Self-adjusting |
| Example 3 | 174 g | (1.71 N) | 24 | Self-adjusting |

EXAMPLE 5

Several hearing protectors are fabricated utilizing the PVC headband 1 of Example 1 and pods 20 of the type produced in accordance with Example 3. In the present example, various filler materials 26 are employed to fill the spaces 24 of the capsular elements 22. The resulting protector constructions are audiometrically tested by a single subject, utilizing the test apparatus and procedure of ANSI S3.19. The results of said tests are reported in Table II, following.

TABLE II

| | Attenuation (db) at Various Frequencies (Hz) | | | | | | | | |
|---|---|---|---|---|---|---|---|---|---|
| Pod Filler | f = 125 | 250 | 500 | 1000 | 2000 | 3150 | 4000 | 6300 | 8000 |
| PVC Foam Plug | 28 | 28 | 28 | 30 | 32 | 36 | 36 | 38 | 41 |
| Rapid Recovery Polyurethane Foam Plug | 28 | 26 | 27 | 27 | 26 | 40 | 46 | 45 | 43 |
| Slow Recovery Polyurethane Foam Plug | 25 | 26 | 29 | 30 | 29 | 40 | 39 | 41 | 41 |
| Glass Wool | 27 | 28 | 27 | 27 | 28 | 38 | 41 | 43 | 41 |
| Silicon "Silly Putty" | 27 | 26 | 26 | 26 | 29 | 42 | 42 | 42 | 42 |
| Air | 25 | 24 | 24 | 25 | 32 | 43 | 45 | 46 | 46 |
| Water | 27 | 25 | 22 | 28 | 30 | 43 | 42 | 41 | 42 |

While the invention has been particularly shown and described in the foregoing specification with reference to preferred embodiments thereof, it will be understood by those skilled in the art that various changes in form and details may be made therein without departing from the essential spirit and the scope of the invention as defined by the appended claims.

The embodiments of the invention in which an exclusive property or privilege is claimed are defined as follows:

1. In a hearing protector of the type comprising a generally U-shaped spring headband having affixed to each of the opposed end portions thereof an inwardly directed ear canal contacting member, each said member having a first end portion adapted to be urged by said spring headband into ear canal obturating relationship and an opposite second end portion having external dimensions small enough to be surrounded by the pinna of the ear and being directly connected to a respective opposed end portion of said headband, the improvement which comprises, in combinations:

a. said first end portion of each of said ear canal contacting members comprising a conically shaped obturating element having an included angle between about 20 and 30°, said obturating element having a closed inner end and an open outer end, said inner end of said obturating element being of a size and shape adapted for partial insertion into the ear, said inner end of said obturating element being of a smaller diameter than said outer end of said obturating element, at least that portion of said obturating element which is insertable in the ear comprising a soft, compliant and hollow capsular element, said capsular element being at least partially filled with a compliant or resilient filler material;

b. said second end portion of each of said ear canal contacting members comprising an end closure member secured to said obturating element, said end closure member being in mating relationship with said obturating element, said end closure member having a socket and a passageway to said socket, said passageway having a chamfered surface, said chamfered surface diverging away from said socket, said socket extending interiorly of said open outer end of said obturating element so as to lessen the tendency for the ear canal contacting members to fold upon themselves;

c. said opposed end portions of said headband each having an inwardly directed segment with a terminal ball element at its end; and d. an articulated fixation connecting each said socket element of each said end closure member to respective ball elements of said headband, thereby to allow said ear canal contacting members to tilt about their point of articulated fixation and to conform to the ear under the urging of said headband, each said articulated fixation having a center point centrally located within said end closure member, said chamfered surface defining a conical stop surface for limiting the extent to which said ear canal contacting members can be tilted.

2. The hearing protector of claim 1 wherein the material of construction of said capsular element has a Shore A hardness, as determined by ANSI-ASTM D 2240-75, of between about 1 and about 50.

3. The hearing protector of claim 1 wherein said filler material is an externally plasticized, polyvinylchloride foam, the nature and concentration of the plasticizer content thereof being such as to provide said foam with the characteristics of slow recovery rate from deformation thereof and low exerted recovery pressure under conditions of deformation.

4. The hearing protector of claim 1 wherein the space within said hollow capsular element is hermetically sealed and is at least partially filled with a fluid.

5. The hearing protector of claim 1 wherein said capsular element is composed of silicone rubber.

6. The hearing protector of claim 1 wherein said capsular element is composed of polyvinylchloride.

7. The hearing protector of claim 1 wherein the inwardly directed recovery biasing force generated by said spring headband at a spacing of 14.35 cm between the opposed end portions thereof is between about 100 and 200 g.

8. The hearing protector of claim 1 wherein said headband is composed of a rigid polyvinylchloride resin.

9. The hearing protector of claim 1 wherein said headband is composed of a polyacetal resin.

* * * * *